United States Patent
Gueffroy

(10) Patent No.: US 7,754,060 B2
(45) Date of Patent: Jul. 13, 2010

(54) ELECTROPHORESIS CASSETTE WITH COLLAPSIBLE BUFFER CHAMBER

(75) Inventor: Donald E. Gueffroy, Davis, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 852 days.

(21) Appl. No.: 11/400,692

(22) Filed: Apr. 7, 2006

(65) Prior Publication Data
US 2007/0235337 A1    Oct. 11, 2007

(51) Int. Cl.
*G01N 27/453*    (2006.01)
(52) U.S. Cl. .................................. 204/618; 204/616
(58) Field of Classification Search ............... 204/606, 204/600, 193, 616, 618, 466, 467
See application file for complete search history.

(56) References Cited

U.S. PATENT DOCUMENTS

| | | | |
|---|---|---|---|
| 4,549,673 A * | 10/1985 | Kupersmit | ............. 229/117.02 |
| 4,574,040 A | 3/1986 | Delony et al. | |
| 5,073,246 A | 12/1991 | Chu et al. | |
| 5,562,812 A * | 10/1996 | Carlson et al. | ............... 204/600 |
| 5,656,145 A | 8/1997 | Nguyen et al. | |
| 2003/0070703 A1* | 4/2003 | Zheng | ......................... 135/126 |

OTHER PUBLICATIONS

Clifton, Michael J., "Protein Separation by Continuous-Flow ELectrophoresis in Microgravity." AIChE Journal vol. 42, No. 7, pp. 2069-2079. Jul. 1996.*

* cited by examiner

*Primary Examiner*—Alex Noguerola
(74) *Attorney, Agent, or Firm*—Townsend and Townsend and Crew LLP.; M. Henry Heines

(57) ABSTRACT

A slab gel electrophoresis cassette with an integrated upper buffer chamber is constructed such that the integrated chamber is collapsible to allow the cassette to assume a reduced thickness for purposes of stacking during storage and shipping.

6 Claims, 2 Drawing Sheets

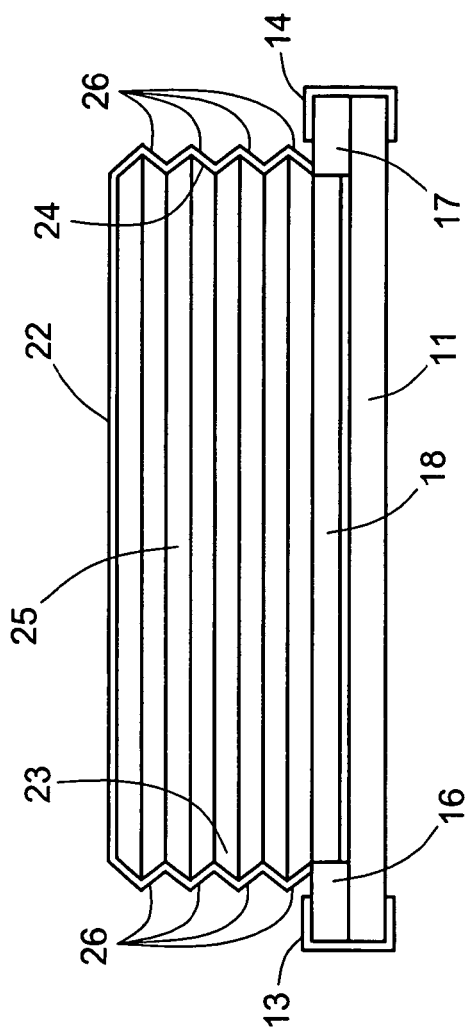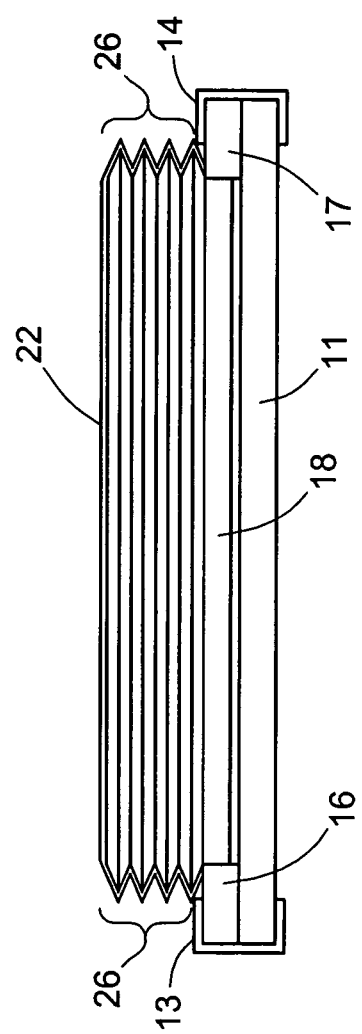

ELECTROPHORESIS CASSETTE WITH COLLAPSIBLE BUFFER CHAMBER

BACKGROUND OF THE INVENTION

1. Field of the Invention

This invention resides in the field of cassettes containing slab-shaped gels for use in electrophoresis.

2. Description of the Prior Art

Slab gel electrophoresis is widely used in clinical and research laboratories for the analysis of biological samples in view of the ability of the procedure to separate and analyze a multitude of samples simultaneously, and the ease with which the separated components of any given sample can be observed and identified by their locations in the gel. The slab-shaped gels that serve as the separation medium in these procedures are often supplied in pre-cast form in a cassette, in which the gel is retained between two flat, usually transparent plates. Pre-cast gels eliminate the risk of operator error in the casting of the gel, and in general the variations that arise when the gels are prepared on an individual basis by the user or at the site where the gels are to be used. The use of pre-cast gels also reduces the time and labor required in the preparation for and performance of an electrophoretic separation.

In use, the cassette is placed in contact with electrodes through buffer solutions that provide full fluid contact with the gel along opposing edges of the gel. While the buffer solutions and the cell that supplies the electrical connections to the gel through the solutions are not part of the cassette, certain cassettes are constructed with an integrated reservoir whose cavity borders an exposed edge of the gel, so that a buffer solution can be placed in the reservoir to contact the gel edge without contacting other edges of the gel. Typically, a single such reservoir is located along the upper edge of the cassette to provide electrical contact with the upper edge of the gel, while electrical contact with the lower edge of the gel is achieved by submerging the lower edge of the cassette in a pool of buffer solution in a tank. The upper and lower buffer solutions are thus fully separated, and electrodes submerged in the solutions supply the electrical potential that spans the gel uniformly along the width of the gel. A description and depiction of a cassette with an integrated upper buffer chamber of this type is found in Chu, D. Y., et al., U.S. Pat. No. 5,073,246, issued Dec. 17, 1991, and incorporated herein by reference. The integrated reservoir, in addition to accommodating the buffer solution, also accommodates the electrode that is immersed in the solution, and in many cases also provides access by which the "comb" or well-forming insert is placed along the upper edge of the gel space to form wells in the gel as the gel is being formed from the monomer solution.

Pre-cast gel cassettes are typically stored in refrigerated environments, and although they are most often oriented vertically during an electrophoretic procedure, they are typically stored horizontally in stacks in laboratory refrigerators. Regardless of whether the cassettes are laid horizontally or allowed to stand vertically, the integrated upper buffer chambers make stacking difficult and consume storage space which is typically at a premium in a laboratory refrigerator. The added volume consumed by an integrated chamber is evident from the figures and description in Chu et al. referenced above, and is likewise evident in certain commercially sold cassettes, notably Bio-Rad CRITERION® cassettes and precast gels. The present invention addresses this problem.

SUMMARY OF THE INVENTION

A cassette of reduced profile that still offers the full benefit of an upper buffer chamber integrated into the cassette construction is achieved in accordance with the present invention by constructing the chamber as a collapsible reservoir that can be collapsed to a reduced depth for purposes of packaging, stacking, storage, and shipping, and expanded to full depth when ready for use. The collapsible nature of the reservoir can be achieved by a single fold or pleat in each of the side walls of the reservoir or by accordion-style pleats in the side walls. In either case, the reservoir is preferably an open-top reservoir yet fully liquid retentive. Preferred reservoirs are rectangular in shape and greater in height and width than in depth, formed from a flat rectangular plate joined to the remainder of the cassette by side walls and a base wall, the side walls and base wall providing the reservoir with its collapsible feature. An optional feature of the reservoir is a resilient construction such that the reservoir will only be collapsed when compressed by an external force, such as by a stacking weight or by constrictive packaging, and once released will return to its expanded condition.

Further features, options, objects, and advantages of the invention will be apparent from the description that follows.

BRIEF DESCRIPTION OF THE DRAWINGS

FIG. 2 is a top view of the cassette of FIG. 1, showing the upper buffer chamber in an expanded state.

FIG. 3 is the same top view as FIG. 2 except with the upper buffer chamber in a collapsed state.

DETAILED DESCRIPTION OF THE INVENTION AND PREFERRED EMBODIMENTS

Figure 1:
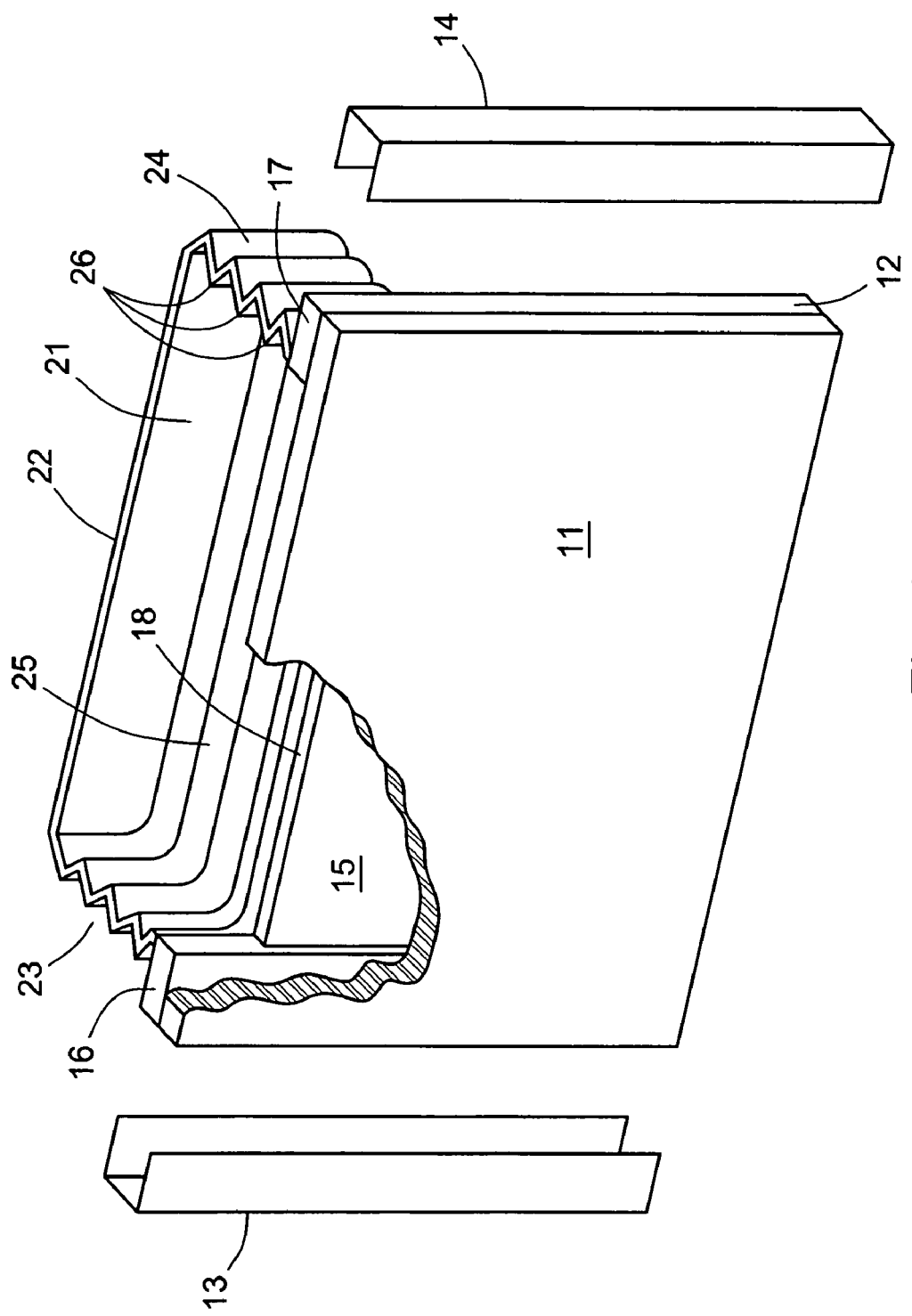
FIG. 1 is a perspective view of a slab gel cassette in accordance with the present invention, with a portion of the cassette broken away to reveal the internal surfaces of the cassette and the gel space.

While the features defining this invention are capable of implementation in a variety of constructions, the invention as a whole will be best understood by a detailed examination of a specific embodiment. One such embodiment is shown in the drawings.

The perspective view of FIG. 1 shows an electrophoresis cassette in partially assembled condition. The cassette is constructed from two plates which, according to the view shown in the Figure, will be designated a front plate 11 and a back plate 12. The two plates are held together by end clamps 13, 14 which are represented in the Figure by simplified structures but in typical units currently available are either more complex or eliminated entirely and replaced by chemical bonds along the edges of the two plates. The front plate 11 in this embodiment is flat and planar while the back plate 12 has a flat and planar central section 15 bordered along both side edges with edge segments 16, 17 that are slightly thicker than the central section 15 such that the central section 15 is slightly recessed relative to the edge segments. This provides the back plate 12 with a stepped profile and leaves a thin slab-shaped gap between the front plate 11 and the central section 15 of the back plate. This gap forms the space for the gel. The bottom edge of the gap is left open for contact with a lower buffer solution when the bottom edge of the cassette is immersed in a tank of the solution. In the back plate 12, the upper edge 18 of the central section 15 is shorter than both the front plate 11 and the edge sections 16, 17. The gel (not shown) that is cast inside the gap terminates at the upper edge 18 of the central section, leaving the upper edge of the gel exposed.

As in the prior art, and notably the Chu et al. patent referenced above, contact of the upper edge 18 of the gel with an electrode through a buffer solution is achieved by an upper buffer chamber 21 integrated into the construction of the back plate 12. The chamber is a reservoir formed by a section of wall extending outward from the plane of the flat central section 15 and the side edges 16. The outwardly extending wall includes a flat section 22 as the rearmost section of the reservoir, joined to the remainder of the back plate 12 by side walls 23, 24 and a base wall 25. The side walls and base wall are formed into accordion-style pleats 26 that allow the reservoir to expand and contract in the manner of a bellows.

Top views of the cassette are shown in FIGS. 2 and 3. In FIG. 2, the pleats 26 are expanded to increase the volume of the reservoir so that it will receive a buffer solution and an upper electrode and thereby serve as an upper buffer chamber, while in FIG. 3 the pleats 26 are fully folded, collapsing the side walls and base wall of the chamber (prior to being filled with buffer solution and having an electrode immersed in the solution) to reduce the thickness of the cassette for stacking.

Although the embodiment shown in these Figures contains a plurality of pleats 26, the collapsible character of the reservoir can be achieved by as few as a single pleat or by any similarly collapsible structure. As noted above, the collapsible walls in certain embodiments of this invention can be given a resilient construction, either by treating the pleats chemically or physically, or by adding spring-loaded supports such as an internal or external frame. A convenient resilient construction is one which when released assumes the open configuration shown in FIG. 2 and assumes the closed configuration shown in FIG. 3 only when compressed by an external force. The closed configuration can for example be achieved by wrapping or enclosing the cassette in packaging material, allowing the reservoir to expand by simply removing the cassette from the packaging.

Referring to FIG. 1, the reservoir 21 and remaining segments of the back plate 12 can be formed as a unitary piece by injection molding in a single mold. Alternatively, the reservoir 21 can be formed as one piece and the remaining segments, including the central section 15 and the two edge sections 16, 17 can be molded as separate pieces and bonded together after molding. In the embodiment shown in the Figures, the corners of the reservoir 21 where the side walls 23, 24 join the base wall 25, are curved. Alternatively, these corners can be sharp angles, such as a right angle. The materials of construction can vary widely and are not critical to the invention provided that they are inert to the chemicals and solvents with which they will come into contact during an electrophoresis procedure. For most applications, elastomers in general can be used. Preferred elastomers include polyethylenes, polypropylenes, and nylons.

Cassettes of the present invention are useful in a variety of applications, but particularly so for pre-cast gels since such gels are often stored under refrigeration until ready for use.

While the foregoing description describes various alternatives to the components shown in the Figures, still further alternatives that fall within the scope of the invention will be readily apparent to those skilled in the art.

What is claimed is:

1. In a slab gel cassette for vertical slab gel electrophoresis comprising first and second plates and spacing means therebetween to define a slab-shaped space, said first plate further comprising a protruding portion along one edge of said first plate, defined as an upper edge, to form a liquid reservoir above and opening into said slab-shaped space, said reservoir being of expanded depth relative to said slab-shaped space for use as an upper buffer chamber, the improvement in which said liquid reservoir is collapsible to reduce the depth of said reservoir when not in use.

2. The slab gel cassette of claim 1 wherein said protruding portion of said first plate comprises a planar wall segment joined to the remainder of said first plate by side walls and a base wall, and said side walls and base wall are each formed with at least one pleat that can be opened and closed.

3. The slab gel cassette of claim 2 wherein said side walls and base wall are each formed with a plurality of pleats that can be opened and closed.

4. The slab gel cassette of claim 1 wherein said liquid reservoir is collapsible when compressed by an external force and resilient to return to an expanded condition upon release from said external force.

5. The slab gel cassette of claim 1 wherein said protruding portion is formed of an elastomer.

6. The slab gel cassette of claim 1 wherein said protruding portion is formed of an elastomer selected from the group consisting of polyethylenes, polypropylenes, and nylons.

* * * * *